United States Patent
McLaren et al.

(10) Patent No.: US 12,091,704 B2
(45) Date of Patent: Sep. 17, 2024

(54) DETECTION, TREATMENT, AND MONITORING OF MICROBIOME-INDUCED METABOLIC DYSFUNCTION

(71) Applicant: McPharma Biotech Inc., Carberry (CA)

(72) Inventors: Derek McLaren, Carberry (CA); Earl McLaren, Carberry (CA)

(73) Assignee: McPharma Biotech Inc., Carberry (CA)

( * ) Notice: Subject to any disclaimer, the term of this patent is extended or adjusted under 35 U.S.C. 154(b) by 854 days.

(21) Appl. No.: 17/271,291

(22) PCT Filed: Sep. 12, 2019

(86) PCT No.: PCT/CA2019/051293
§ 371 (c)(1),
(2) Date: Feb. 25, 2021

(87) PCT Pub. No.: WO2020/056494
PCT Pub. Date: Mar. 26, 2020

(65) Prior Publication Data
US 2021/0340590 A1    Nov. 4, 2021

Related U.S. Application Data

(60) Provisional application No. 63/732,626, filed on Sep. 18, 2018.

(51) Int. Cl.
| | |
|---|---|
| *C12Q 1/06* | (2006.01) |
| *G01N 33/49* | (2006.01) |
| *G01N 33/569* | (2006.01) |

(52) U.S. Cl.
CPC .............. *C12Q 1/06* (2013.01); *G01N 33/49* (2013.01); *G01N 33/56911* (2013.01)

(58) Field of Classification Search
None
See application file for complete search history.

(56) References Cited

FOREIGN PATENT DOCUMENTS

| | | |
|---|---|---|
| WO | 2012024638 | 2/2012 |
| WO | 20013130773 | 9/2013 |

OTHER PUBLICATIONS

J.R. Bush M.J. Alfa (2018): "Decreasing levels of Sporacetigenium correlate with improved diabetic parameters in healthy adults consuming MSPrebotic digestion resistant starch." The Journal of Aging Research and Clinical Practice, whole document.
Yang, Junyi "Influence of dietary fibers and whole grains on fecal microbiota during in vitro fermentation." Dissertations, Theses, & Student Research in Food Science and Technology Department, 2012. p. 57; table 2.4.
Cox, Laura M., Cho, Ilseung, Young, Scott A., et al. "The nonfermentable dietary fiber hydroxypropyl methylcellulose modulates intestinal microbiota." The FASEB Journal, 2013, vol. 27, No. 2, p. 692-702.
Nobel, Yael R., Cox Laura M., Kirigin Francis F., et al. "Metabolic and metagenomic outcomes from early-life pulsed antibiotic treatment." Nature communications, 2015, vol. 6, p. 7486.
A. Everard et al: "Responses of Gut Microbiota and Glucose and Lipid Metabolism to Prebiotics in Genetic Obese and Diet-Induced Leptin-Resistant Mice", Diabetes, vol. 60, No. 11, Sep. 20, 2011, pp. 2775-2786, ISSN: 0012-1797.
Michelle J. Alfa et al: "A Radomized Placebo Controlled Clinical Trial to Determine the Impact of Digestion Resistant Starch MSPrebiotic ®: on Glucose, Insulin, and Insulin Resistance in Elderly and Mid-Age Adults", Frontiers in Medicine, vol. 4, Jan. 22, 2018.

*Primary Examiner* — Oluwatosin A Ogunbiyi
(74) *Attorney, Agent, or Firm* — Michael R Williams; Ryan W Dupuis; Ade & Company Inc.

(57) ABSTRACT

Individuals consuming a prebiotic and who displayed improvements in blood glucose and/or insulin levels also displayed a decrease in the levels of the non-butyrate-producing Firmicutes genus of bacteria *Sporacetigenium*. Increasing levels of butyrate-producing Firmicutes genera were not consistently correlated with improvements in metabolism in response to prebiotic consumption. In the general population, *Sporacetigenium* levels are positively correlated with insulin levels.

19 Claims, 4 Drawing Sheets

DETECTION, TREATMENT, AND MONITORING OF MICROBIOME-INDUCED METABOLIC DYSFUNCTION

PRIOR APPLICATION INFORMATION

The instant application is a 371 of PCT Application CA2019/051293, which claimed the benefit of U.S. Provisional Patent Application Ser. No. 62/732,626, filed Sep. 18, 2018 and entitled "DETECTION, TREATMENT, AND MONITORING OF MICROBIOME-INDUCED METABOLIC DYSFUNCTION", the entire contents of which are incorporated herein by reference for all purposes.

BACKGROUND OF THE INVENTION

The gut microbiome consists of the microbial community found in the small and large intestines. The normal composition of the healthy human gut microbiome detected in excreted feces contains five main phyla: Actinobacteria, Bacteroidetes, Firmicutes, Proteobacteria, and Verrucomicrobia, containing somewhere between 500 and 1000 discrete species. While we can now identify gut microbiota to genus or species levels (Schloss et al. 2009), our understanding of their functional activities remains limited. One activity that is well appreciated is the ability of select microbiota to break down carbohydrates that go undigested by the host's digestive system, also known as prebiotics, to provide energy in the form of short chain fatty acids (SCFAs) and nutrition. It is estimated that SCFAs can meet approximately 5-10% of the body's total energy demands in humans (Royall et al. 1990).

In addition to providing energy, this complex, symbiotic microbial ecosystem interacts with the gastrointestinal tract, providing key metabolic end-products that are essential to the health of the host (Holmes 2012, Topping 2001, Ze 2012, Belenguer 2006, Flint 2012, Cecchini 2013, Pokusaeva 2011). The gut microbiome influences many important functions including: gut integrity, immune function, bile and lipid metabolism, various organ functions (i.e. heart, liver, brain, etc.), and susceptibility to infections of the gastrointestinal tract (Brown 2012, Holmes 2012, Malaguarnera 2012, Toward 2012, Hardy 2013, Topping 2001).

Both Bacteroidetes and Firmicutes are producers of SCFAs, with *Bacteroides* bacteria generally producing acetate and propionate, and Firmicutes bacteria generally producing butyrate (Macfarlane and Macfarlane. 2003). Butyrate is both an energy source and a multifunctional signaling molecule, helping mediate dietary influences on various physiological processes (Holscher. 2017, Rowland et al. 2018). Specifically, butyrate stimulates release of glucagon-like peptide-1 (GLP-1), a potent insulinotropic incretin produced by enteroendocrine L-cells in the intestines (Lin et al. 2016). Previous studies have linked increasing dietary prebiotics to elevated GLP-1 levels and improved diabetic parameters (Rideout et al. 2017), but the role between specific gut microbe genera, including those belonging to phylum Firmicutes, and diabetic parameters remains largely unexplored (FIG. 1).

The impact of age-related gut microbiome changes on human health is well-studied (Mariat et al. 2009) and the importance of *Bifidobacterium* and Lactobacilli abundance in maintaining gut health is known. We previously demonstrated that consumption of prebiotic MSPrebiotic® digestion resistant potato starch (DRS) stimulated the growth of *Bifidobacterium*, decreased *E. coli/Shigella* species, increased butyrate, and improved blood glucose, insulin, and insulin resistance levels in the elderly (Alfa et al. 2018a, Alfa et al. 2018b). While *Bifidobacterium* (phylum Actinobacteria) are potent DRS fermenters, they do not produce butyrate, and we concluded that increased levels of butyrate in feces of ELD consuming DRS were likely due to cross-feeding that stimulated Firmicutes bacteria (Cockburn. 2016, Holscher. 2017, Alfa et al. 2018a). This may be an "age-related" or "prebiotic-specific" phenomenon, as increasing *Bifidobacterium* abundance with galactooligosaccharides (GOS) did not translate to improved insulin resistance in obese prediabetics with a mean age of 59 years (Canfora et al. 2017).

We sought to determine if specific changes in Firmicutes genera of the gut microbiome correlated with the blood glucose or insulin changes previously identified in ELD consuming DRS and whether these correlations held up in the MID population consuming DRS. Surprisingly, we did not detect a correlation between butyrate-producing Firmicutes and metabolic improvements. However, we discovered a signal of gut microbiome change associated with metabolic improvements in response to DRS consumption in all populations studied.

SUMMARY OF THE INVENTION

According to an aspect of the invention, there is provided a method for determining efficacy of a gut microbiome modulating treatment for high blood glucose or high blood insulin levels in an individual at risk of developing or who has developed or who has type 2 diabetes, said method comprising:
  detecting *Sporacetigenium* levels in a first gut microbiome sample from the individual at a first time point;
  administering to the individual a microbiome modulating treatment on a dosage regimen for a suitable period of time;
  following the suitable period of time, obtaining a second gut microbiome sample from the individual;
  detecting *Sporacetigenium* levels in the second sample; and
  comparing *Sporacetigenium* levels in the second gut microbiome sample to *Sporacetigenium* levels in the first gut microbiome sample,
  wherein if the *Sporacetigenium* levels in the second sample are lower than *Sporacetigenium* levels in the first sample, continuing the dosage regimen for the individual.

In some embodiments, at the first time point and the second time point, at least one type 2 diabetes related parameter of the individual is measured and these two measurements are also compared.

According to another aspect of the invention, there is provided a method for determining efficacy of a microbiome modulating treatment for high blood glucose or high blood insulin levels in an individual at risk of developing or who has developed or who has type 2 diabetes, said method comprising:
  detecting *Sporacetigenium* levels in a first gut microbiome sample from the individual at a first time point;
  determining a first measurement of a type 2 diabetes related parameter of the individual at the first time point;
  administering to the individual a microbiome modulating treatment on a dosage regimen for a suitable period of time;
  following the suitable period of time, obtaining a second gut microbiome sample from the individual;

detecting *Sporacetigenium* levels in the second sample;
determining a second measurement of the type 2 diabetes related parameter of the individual at the second time point;
comparing *Sporacetigenium* levels in the second gut microbiome sample to *Sporacetigenium* levels in the first gut microbiome sample, and
comparing the first measurement of the type 2 diabetes related parameter and the second measurement of the type 2 diabetes related parameter,
wherein if the *Sporacetigenium* levels in the second sample are lower than *Sporacetigenium* levels in the first sample and the second type 2 diabetes related parameter is lower than the first type 2 diabetes related parameter, continuing the dosage regimen for the individual.

In some embodiments, the gut microbiome sample is, for example but by no means limited to, a stool or fecal sample or colonic contents, whether sampled in situ or via intervention.

In some embodiments, the microbiome modulating treatment is a microbiome therapy, that is, a treatment that is known to or expected to alter the microbiome of the individual. Examples of microbiome therapies are discussed herein and other examples will be readily apparent to one of skill in the art.

According to another aspect of the invention, there is provided a method for detecting the signature of an altered gut microbiome (also known as dysbiosis) that is correlated with impaired blood glucose and/or insulin homeostasis in an individual comprising the monitoring of *Sporacetigenium* levels and predicting the efficacy of microbiome therapies if *Sporacetigenium* is present.

As will be appreciated by one of skill in the art, *Sporacetigenium* may be detected in a sample by a variety of means, which will be readily apparent to one of skill in the art. Illustrative examples are provided below.

In some embodiments of the invention, *Sporacetigenium* is detected by directed 16S V4 ribosomal subunit amplification (for example, Real-Time Polymerase Chain Reaction; RT-PCR or Quantitative PCR; qPCR) of *Sporacetigenium* using the abundance of *Blautia* or other common commensal unrelated to blood glucose or insulin regulation as the reference value. As will be apparent to one of skill in the art, *Blautia* is both common (found in most gut microbiomes) and abundant (making up a large proportion of each microbiome), and accordingly is suitable to be used as an internal control. However, other suitable candidates for use as an internal control will be readily apparent to one of skill in the art.

In another embodiment of the invention, *Sporacetigenium* is detected by whole microbiome sequencing using the 16S V4 ribosomal subunit and/or other relevant regions.

In another embodiment of the invention, *Sporacetigenium* is detected by shotgun metagenome sequencing, or another suitable unbiased genomic-based approach, or any method that reports proportional representation of *Sporacetigenium* in the microbiome.

In some embodiments of the invention, the individual has high insulin (hyperinsulinemia; about 9 uIU/L or higher, or as determined or diagnosed by a physician) and/or high fasting blood glucose (hyperglycemia; about 5.6 mmol/L or higher, or as determined or diagnosed by a physician) and/or high insulin resistance and/or high HbA1C (glycated hemoglobin; about 5.5% (about 37 mmol/mol) or higher, or as determined or diagnosed by a physician).

In another embodiment of the invention, the individual is at risk of developing Type 2 Diabetes (T2D) due to family history or lifestyle factors.

In another embodiment of the invention, the individual has pre-diabetes (elevated fasting blood glucose levels higher than normal but below 6.0 mmol/L).

In another embodiment of the invention, the individual has been diagnosed with or is suspected of having T2D.

In some embodiments of the invention, the microbiome therapy is a prebiotic, administered daily or as needed, for as long as the metabolic markers continue to show improvement compared to baseline levels.

As discussed herein, the prebiotic microbiome therapeutic may be digestion resistant starch from potatoes or resistant potato starch, delivered daily or as needed, for as long as the metabolic markers continue to show improvement compared to baseline levels.

As discussed herein, the effective amount may be for example 2 to 40 g, 2 to 30 g, 2 to 20 g, 5 to 40 g, 5 to 30 g, 5 g to 20 g, or 10 to 20 g of resistant potato starch.

In another embodiment of the invention, the microbiome therapy is a probiotic, administered daily or as needed, for as long as the metabolic markers continue to show improvement compared to baseline levels.

In another embodiment of the invention, the microbiome therapy is an antibiotic, administered daily or as needed, for as long as the metabolic markers continue to show improvement compared to baseline levels.

In another embodiment of the invention, the microbiome therapy is a combination of prebiotics, and/or probiotics, and/or antibiotics, and/or bacteriophages, administered daily or as needed, for as long as the metabolic markers continue to show improvement compared to baseline levels.

DESCRIPTION OF THE PREFERRED EMBODIMENTS

Figure 1:
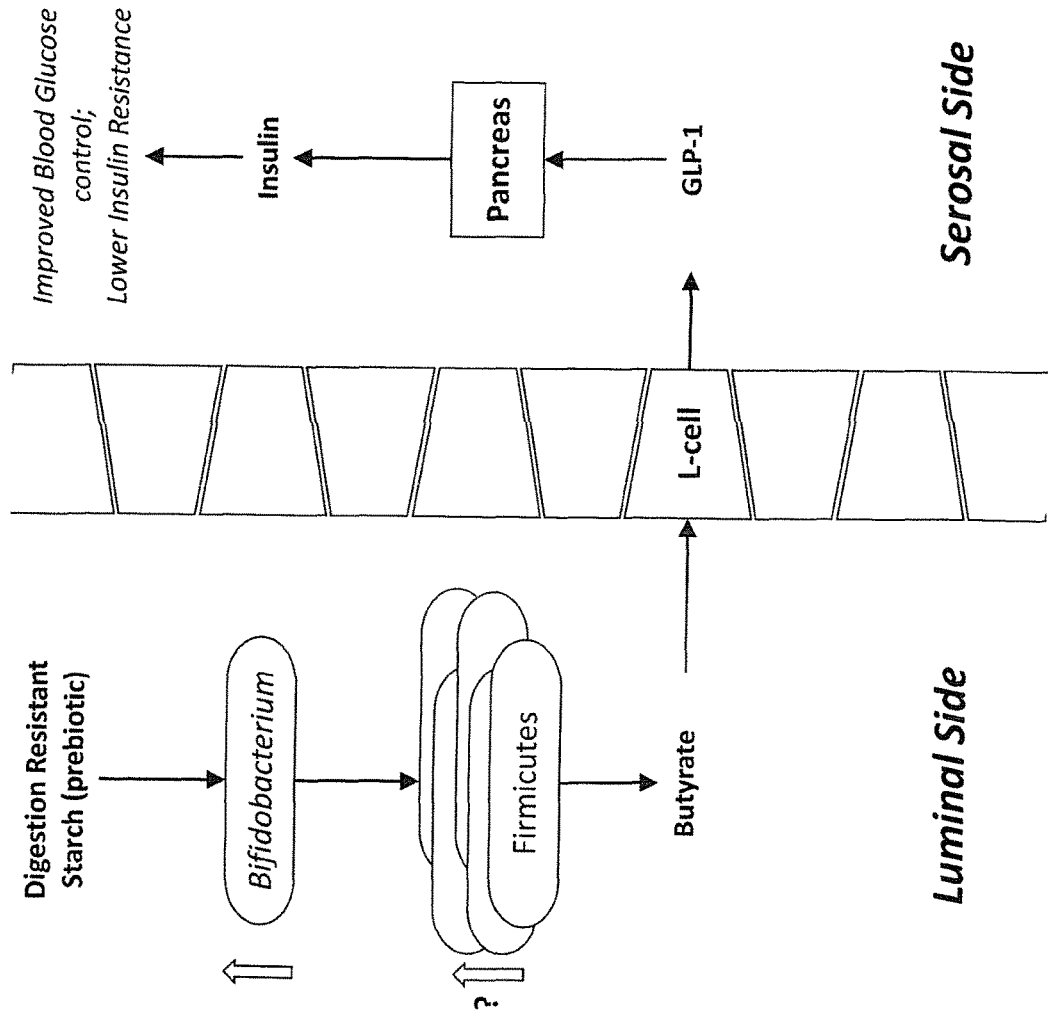
FIG. 1. Canonical mechanism of prebiotic fermentation leading to improved metabolic parameters via butyrate-producing Firmicutes bacteria. Prebiotic utilization by the gut microbial ecosystem promotes improved insulin regulation and blood glucose control. Prebiotics are fermented at the primary level by bacterial species such as *Bifidobacterium* and the degradation products become 'food' for bacteria at the secondary level, including those belonging to phylum Firmicutes. Various Firmicutes bacteria produce the short chain fatty acid butyrate, which acts on enteroendocrine cells (ie. L-cells) in the intestinal wall, resulting in increased production of glucagon-like peptide-1 (GLP-1). The pancreas senses GLP-1, leading to improved insulin secretion and reductions in insulin resistance. Whether prebiotic fermentation by *Bifidobacterium* stimulates a specific genus of butyrate-producing Firmicutes bacteria during this process remains unknown.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

We investigated the correlation between improvements in metabolic parameters and changes in the microbiome in response to supplementation with prebiotic resistant potato starch (MSPrebiotic®).

MSP Starch Products Inc. manufactures MSPrebiotic® Resistant Potato Starch, an unmodified type 2 resistant starch (RS2) that is a *Solanum tuberosum* extract preparation of food grade quality for animal and human food application. Resistant potato starch is also referred to as digestion or digestive resistant starch (DRS). While MSPrebiotic®, which contains 7 g of fiber in 10 g of product is used in the trials and experiments discussed herein, it is important to note that as discussed herein, another suitable resistant potato starch or potato resistant starch, that is, another unmodified RS type 2 potato starch, comprising at least 60% resistant starch or at least 65% resistant starch or at least 70% resistant starch or at least 75% resistant starch or at least 80% resistant starch of total extract or total potato extract may be used. That is, the extract itself may comprise at least 60% resistant starch, at least 65% resistant starch, at least 70% resistant starch, at least 75% resistant starch or at least 80% resistant starch on a weight to weight basis.

According to an aspect of the invention, there is provided a method lot determining efficacy of a gut microbiome modulating treatment for high blood glucose or high blood insulin levels in an individual at risk of developing or who has developed or who has type 2 diabetes, said method comprising:
  detecting *Sporacetigenium* levels in a first gut microbiome sample from the individual at a first time point;
  administering to the individual a gut microbiome modulating treatment on a dosage regimen fora suitable period of time;
  following the suitable period of time, obtaining a second gut microbiome sample from the individual;
  detecting *Sporacetigenium* levels in the second sample; and
  comparing *Sporacetigenium* levels in the second gut microbiome sample to *Sporacetigenium* levels in the first gut microbiome sample, wherein if the *Sporacetigenium* levels in the second sample are lower than *Sporacetigenium* levels in the first sample, continuing the dosage regimen for the individual.

In some embodiments, at the first time point and the second time point, at least one type 2 diabetes related parameter of the individual is measured and these two measurements are also compared.

According to another aspect of the invention, there is provided a method for determining efficacy of a gut microbiome modulating treatment for high blood glucose or high blood insulin levels in an individual at risk of developing type 2 diabetes, said method comprising:
  detecting *Sporacetigenium* levels in a first gut microbiome sample from the individual at a first time point;
  determining a first measurement of a type 2 diabetes related parameter of the individual at the first time point;
  administering to the individual a gut microbiome modulating treatment on a dosage regimen or schedule for a suitable period of time;
  following the suitable period of time, obtaining a second gut microbiome sample from the individual;
  detecting *Sporacetigenium* levels in the second sample;
  determining a second measurement of the type 2 diabetes related parameter of the individual at the second time point;
  comparing *Sporacetigenium* levels in the second gut microbiome sample to *Sporacetigenium* levels in the first gut microbiome sample, and
  comparing the first measurement of the type 2 diabetes related parameter and the second measurement of the type 2 diabetes related parameter,
  wherein if the *Sporacetigenium* levels in the second sample are lower than *Sporacetigenium* levels in the first sample and the second measurement of the type 2 diabetes related parameter is lower than the first measurement of the type 2 diabetes related parameter, continuing the dosage regimen for the individual.

It is of note that while it may be more convenient to obtain samples for *Sporacetigenium* and type 2 diabetes related parameter measurements at the same time, this is not a requirement of the invention. That is, the samples do not necessarily need to be taken at exactly the same time, but may be taken separately within a reasonable time period and still be considered as having been taken at either the first time point or the second time point as the case may be.

Similarly, the measuring of the samples does not need to be done immediately or even by the same institution. That is, means for storing suitable samples for measurement of bacterial levels or type 2 diabetes related parameters are well known in the art.

The individual who is at risk of developing type 2 diabetes may be at risk based on genetic predisposition, familial history, heredity, lifestyle and/or one or more type 2 diabetes related parameters being elevated, for example, fasting blood glucose levels, insulin resistance levels, insulin levels, and/or HbA1C levels. As discussed above, the individual may also be an individual who has type 2 diabetes, that is, an individual who has been diagnosed with type 2 diabetes. Similarly, the individual may be an individual who has developed type 2 diabetes, that is, an individual who has recently developed type 2 diabetes and who may or may not have been diagnosed with type 2 diabetes.

According to another aspect of the invention, there is provided a method for determining efficacy of a gut microbiome modulating treatment for high blood glucose or high blood insulin levels in an individual being administered said microbiome modulating treatment, said method comprising:
detecting *Sporacetigenium* levels in a first gut microbiome sample from the individual at a first time point;
following a suitable period of time, obtaining a second gut microbiome sample from the individual;
detecting *Sporacetigenium* levels in the second sample; and
comparing *Sporacetigenium* levels in the second gut microbiome sample to *Sporacetigenium* levels in the first gut microbiome sample,
wherein if the *Sporacetigenium* levels in the second sample are lower than *Sporacetigenium* levels in the first sample, the microbiome modulating treatment is effective. If this is the case, the treatment, that is, the dosage regimen, is continued.

According to another aspect of the invention, there is provided a method for determining efficacy of a gut microbiome modulating treatment for high blood glucose or high blood insulin levels in an individual being administered said microbiome modulating treatment, said method comprising:
detecting *Sporacetigenium* levels in a first gut microbiome sample from the individual at a first time point;
determining a first measurement of a type 2 diabetes related parameter of the individual at the first time point;
following a suitable period of time, obtaining a second gut microbiome sample from the individual;
detecting *Sporacetigenium* levels in the second sample;
determining a second measurement of the type 2 diabetes related parameter of the individual at the second time point;
comparing *Sporacetigenium* levels in the second gut microbiome sample to *Sporacetigenium* levels in the first gut microbiome sample, and
comparing the first measurement of the type 2 diabetes related parameter and the second measurement of the type 2 diabetes related parameter,
wherein if the *Sporacetigenium* levels in the second sample are lower than *Sporacetigenium* levels in the first sample and the second measurement of the type 2 diabetes related parameter is lower than the first measurement of the type 2 diabetes related parameter, the gut microbiome modulating treatment is effective. If that is the case, then the treatment, that is, the dosage regimen, is continued.

As will be appreciated by one of skill in the art, during the suitable period of time as defined above, the individual continues to be administered the gut microbiome modulating treatment.

As discussed herein, we demonstrate a method for detecting and treating individuals with impaired metabolic homeostasis who are sensitive to microbiome-targeted therapeutic intervention using a microbiome modulating compound. In some embodiments, the microbiome modulating compound is prebiotic resistant potato starch.

In other embodiments, the microbiome modulating compound is selected from the group consisting of: resistant potato starch, probiotic genera, species, and strains; prebiotics supporting growth of probiotic genera, species and strains; resistant starch from corn, tapioca, banana, grains, tubers and the like; fructooligosaccharides; galactooligosaccharides; xylooligosaccharides; mannanoligosaccharides; arabinoxylooligosaccharides; arabinogalactan polysaccharides; and galactomannan polysaccharides.

Dietary changes that support the growth of healthy bacteria, including the probiotic bacteria listed above:
Dietary treatments that reduce the availability of glucose and/or fructose and/or other fermentation substrates to *Sporacetigenium* in the digestive tract.
Antibiotics that target *Sporacetigenium* or another bacterium/other bacteria that facilitate the growth of *Sporacetigenium*.

The probiotic genera, species and strains may be selected from the group consisting of: *Bifidobacterium*; *Staphylococcus*; *Clostridium*; Lactobacilli; *Prevotella*; Barnsiella; *Parasutterella*; and combinations thereof; The resistant starch may be RS1, RS2, RS3, RS4, or RS5.

The corn may be high amylose maize.

The grains may be barley, wheat, sorghum, oats or the like.

Examples of suitable fructooligosaccharides include but are by no means limited to inulin and inulin-type fructans.

The galactooligosaccharides may be of varying lengths, for example, between 2 and 8 saccharide units, and may include various linkages of galactose for example but by no means limited to β-(1-4), β-(1-6) galactose, and a terminal glucose.

The Xylooligosaccharides may be composed of xylose or related C5 sugar oligosaccharides.

The mannanoligosaccharides, may be for example glucomannanoligosaccharides.

Suitable galactomannan polysaccharides include guar gum.

In other embodiments, the microbiome modulating compound is selected from the group consisting of: resistant potato starch, probiotic genera, species, and strains; prebiotics supporting growth of probiotic genera, species and strains; resistant starch from corn, tapioca, banana, grains, tubers and the like; fructooligosaccharides; galactooligosaccharides; xylooligosaccharides; mannanoligosaccharides; arabinoxylooligosaccharides; arabinogalactan polysaccharides; galactomannan polysaccharides; dietary changes that support the growth of probiotic bacteria; dietary treatments that reduce the availability of glucose and/or fructose and/or other fermentation substrates to *Sporacetigenium* in the digestive tract; and antibiotics that target *Sporacetigenium* or another bacterium/other bacteria that facilitate the growth of *Sporacetigenium*.

In yet other embodiments, the microbiome modulating compound is selected from the group consisting of: resistant potato starch, probiotic genera, species, and strains; prebiotics supporting growth of probiotic genera, species and strains; resistant starch from corn, tapioca, banana, grains, tubers and the like; fructooligosaccharides; galactooligosaccharides; xylooligosaccharides; mannanoligosaccharides; arabinoxylooligosaccharides; arabinogalactan polysaccharides; galactomannan polysaccharides; dietary changes that support the growth of probiotic bacteria; dietary treatments that reduce the availability of glucose and/or fructose and/or other fermentation substrates to *Sporacetigenium* in the digestive tract; antibiotics that target *Sporacetigenium* or another bacterium/other bacteria that facilitate the growth of *Sporacetigenium*; mixed plant cell wall fibers; beta-glucans; resistant dextrins; resistant maltodextrins; limit dextrins; polydextrose; alginate; pectin polysaccharides; hydroxypropylmethylcellulose; chitin; chondroitin-containing compounds; and glucosamine-containing compounds.

Preferably, the mixed plant cell wall fibers comprise two or more of the following plant cell wall fibers in varying proportions: cellulose, pectin, lignin, beta-glucan, and arabinoxylan regardless of source.

The Beta-glucans may be from cereal, such as for example, mixed-link (1-3, 1-4) beta-glucans from oat, barley, rye, wheat, or the like, or from fungi, for example, yeast, mushroom, and the like, sources Resistant dextrins, resistant maltodextrins, and limit dextrins may be from wheat, corn, or other suitable sources. These non-digestible oligosaccharides of glucose molecules are joined by digestible linkages and non-digestible α-1,2 and α-1,3 linkages.

The polydextrose may be highly branched and may contain α- and β-1-2, 1-3, 1-4 and 1-6 linkages, with the 1-6 linkage predominating in the polymer.

The alginate may be β-1,4-D-mannuronic acid and α-1, 4-L-guluronic acid organized in homopolymeric compounds of either mannuronate or guluronate, or as heteropolymeric compounds, expressed as mannuronic acid to guluronic acid ratio.

The pectin polysaccharides may have a backbone chain of α-(1→4)-linked D-galacturonic acid units interrupted by the insertion of (1→2)-linked L-rhamnopyranosyl residues in adjacent or alternate positions. These compounds are present in cell walls and intracellular tissues of fruits, vegetables, legumes, and nuts.

Hydroxypropylmethylcellulose, also known as Hypromellose, is a propylene glycol ether of methylcellulose containing methoxyl groups and hydroxypropyl group.

The chitin may be from for example from fungi or arthropods.

Suitable chondroitin-containing compounds includes chondroitin sulfate from animal sources.

Suitable glucosamine-containing compounds includes glucosamine sulfate from animal sources.

In some embodiments, the gut microbiome modulating treatment may be or may also include spores from a single strain or specie of bacteria, yeast, or other fungi; bacteriophage or a combination of bacteriophages; or an exogenously produced metabolite or metabolites normally derived from the metabolism of the gut microbiome, also known as postbiotics or parabiotics.

As will be appreciated by one of skill in the art, a type 2 diabetes related parameter as used herein refers to a parameter that is associated with or measured as part of monitoring for type 2 diabetes.

In some embodiments of the invention, the type 2 diabetes related parameter is selected from the group consisting of: insulin levels; fasting blood glucose levels; insulin resistance levels; HbA1C levels.

As discussed herein, high insulin or hyperinsulinemia is generally diagnosed at about 9 uIU/L; high fasting blood glucose or hyperglycemia is generally diagnosed at about 5.6 mmol/L; and high HbA1C is generally diagnosed at about 5.5% or about 37 mmol/mol or higher.

The period of time, that is, the suitable period of time may be for example about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks or longer.

The *Sporacetigenium* levels may be measured using any suitable means known in the art. For example, *Sporacetigenium* levels may be measured using real-time polymerase chain reaction (RT-PCR)-based methods; qualitative PCR (qPCR) based methods; by microbiome sequencing directed at any sequence that defines *Sporacetigenium*, including but not limited to the 16S V4 ribosomal subunit sequence; by shotgun metagenomic sequencing; by quantitative fluorescent in situ hybridization (FISH) with probes recognizing sequence that defines *Sporacetigenium*, including but not limited to the 16S V4 ribosomal subunit sequence; or by antibody or cell-binding based methods.

As will be appreciated by one of skill in the art, the levels of *Sporacetigenium* are being measured over time. Consequently, levels of *Sporacetigenium* may be determined by direct measurement, using suitable means known in the art, for example, such as those discussed above. Alternatively, the level of *Sporacetigenium* in a given sample may be compared to an internal control, for example, using the abundance of *Blautia* or other common commensal unrelated to blood glucose or insulin regulation as the reference value. As will be apparent to one of skill in the art, *Blautia* is both common (found in most gut microbiomes) and abundant (making up a large proportion of each microbiome), and accordingly is suitable to be used as an internal control. However, other suitable candidates for use as an internal control will be readily apparent to one of skill in the art. Alternatively, the control may be a non-biological control. Furthermore, as will be appreciated by one of skill in the art, the control does not necessarily need to be repeated with each measurement.

As will be apparent to those of skill in the art, an "effective amount" of a gut microbiome modulating compound is an amount that is believed to be sufficient to reduce *Sporacetigenium* levels and improve at least one type 2 diabetes related parameter in the individual when administered on a dosage regimen or schedule over the suitable period of time. Such an effective amount will of course depend on the specific gut microbiome modulating compound being administered as well as other factors such as the age, weight, general condition and severity of symptoms of the individual.

As discussed herein, the prebiotic microbiome therapeutic may be resistant potato starch, delivered daily or as needed, for as long as the metabolic markers continue to show improvement compared to baseline levels.

As discussed herein, the effective amount of resistant potato starch may be for example 2 to 40 g, 2 to 30 g, 2 to 20 g, 5 to 40 g, 5 to 30 g, 5 g to 20 g, or 10 to 20 g of resistant potato starch.

The effective amount may be administered in one or more doses during the day.

As used herein, "daily" does not necessarily mean "every day" but may mean 9 out 10 days; 8 out of 9 days; 7 out of 8 days; 6 out of 7 days; 5 out of 6 days; 4 out of 5 days; 3 out of 4 days; 2 out of 3 days; 1 out of 2 days or combinations thereof.

Specifically, we measured the correlations between improvements in metabolic parameters, including change in fasting blood glucose and change in fasting insulin, and changes in general belonging to the phylum Firmicutes in response to supplementation with probiotic resistant potato starch.

Generally, members of the Firmicutes phylum are known to produce butyrate, a multifunctional short chain fatty acid (SOFA) that serves as a source of energy locally for colonocytes and systemically via conversion to β-hydroxybutyryl CoA and entry into the TCA cycle. Butyrate has also been shown to stimulate the release of glucagon-like peptide-1 (GLP-1) from enterocytes in the intestines via free fatty acid receptor (FFAR)-dependent and -independent mechanisms. GLP-1 sensed by the pancreas leads to insulin secretion and improved blood glucose homeostasis. Therefore, interventions that elevate butyrate-producing Firmicutes bacteria are expected to produce correlated improvements in both insulin and blood glucose levels.

However, butyrate is not produced directly from prebiotic fermentation, but rather arises from cross-feeding events in which Firmicutes bacteria break down metabolic end products produced by primary prebiotic-fermenting bacteria such as *Bifidobacterium* of the phylum Actinobacteria. We previously demonstrated that consumption of resistant potato starch led to significant increases in *Bifidobacterium* species, elevated butyrate levels in stool, and improvements in blood glucose, insulin, and insulin resistance in elderly individuals (>70 years or older (ELD); Alfa et al. 2018a, Alfa et al. 2018b). While consumption of resistant potato starch did lead to overall changes in Firmicutes genera, including increases in the elderly and decreases in the middle-aged group (30 to 50 years (MID); Alfa et al 2018a), the relationship between Firmicutes bacteria, resistant potato starch consumption, and the effects on metabolism were unclear (FIG. 1).

Investigating further, we examined correlations between change in blood glucose or change in insulin levels and change in abundance of Firmicutes bacteria in response to consumption of resistant potato starch. We reasoned that correlations between dynamic variables (ie. Changes in levels) would be more informative than correlations between static points (ie. Levels at baseline and levels at the end of the study) because correlations at static points would not necessarily reflect the effects of the treatment. In other words, any correlation between starting or baseline levels of bacteria and blood glucose/insulin level would likely be independent of the effects of microbiome intervention.

Figure 2:
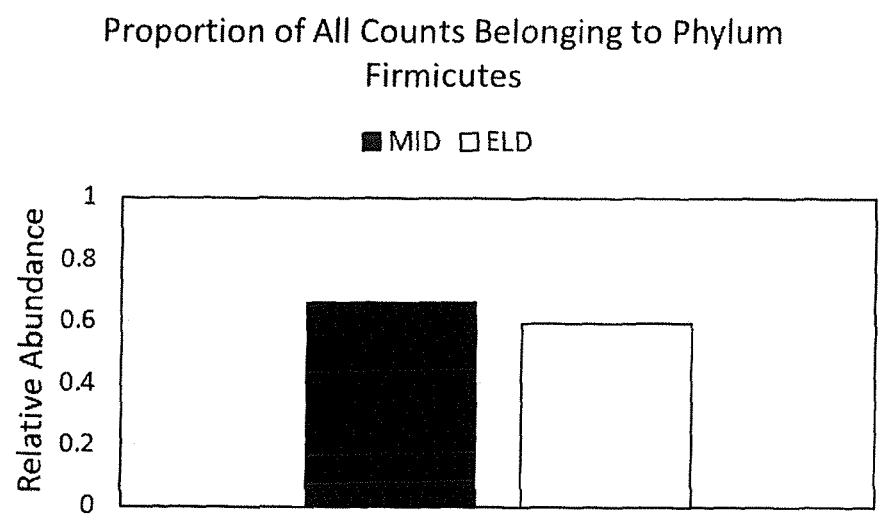
FIG. 2. Proportion of all counts (ie. Sequenced reads) belonging to phylum Firmicutes in both the middle-aged (MID) and elderly (ELD) cohorts at baseline. Firmicutes is one of five phyla found in the healthy gut microbiome, but it accounts for over half of all counts in both MID and ELD cohorts. Specifically, sums of average counts for all Genera belonging to Phylum Firmicutes for the middle-aged (30-50 years, MID; N=40) and elderly cohorts (>70 years, ELD; N=35) as a proportion of all bacteria recorded at baseline, prior to randomization to placebo or MSPrebiotic®. Of the five bacterial phyla known to inhabit the human gut microbiome, Firmicutes is the most abundant, accounting for more than half of all counts in both age groups.

Firmicutes genera were the focus of our study for several reasons. First, Firmicutes genera constituted over 66% of all bacteria in the MID and over 59% of all bacteria in the ELD (FIG. 2). Second, increased butyrate production by members of the Firmicutes phylum was a logical hypothesis for which to explain improved blood glucose, insulin, and insulin resistance in response to prebiotic supplementation based on previous research (FIG. 1). Finally, we gained statistical power using the Benjamini-Hochberg method by focusing on correlations related to the Firmicutes genera detected in our study (Tables 1 and 2).

We previously documented a significant decrease in fasting blood glucose, insulin, and insulin resistance in the ELD consuming resistant potato starch (Alfa et al. 2018b). However, some individuals in the MID group consuming resistant potato starch also showed an improvement in blood glucose despite the overall mean levels not significantly changing (Alfa et al. 2018b). We therefore asked whether there were any Firmicutes genera whose change in levels was significantly correlated with changes in blood glucose by calculating Pearson correlation coefficients (r), and whether there was agreement in correlations between MID and ELD groups consuming resistant potato starch. While we found significant correlations between change in blood glucose and butyrate-producing *Butyricicoccus* in the ELD and butyrate-producing *Roseburia* in the MID, there was no agreement between groups with respect to butyrate producers (Tables 1 and 2).

Surprisingly, we found significant positive correlations between changes in blood glucose and changes in *Sporacetigenium* in both MID and ELD groups consuming resistant potato starch (Tables 1 and 2). In other words, as blood glucose levels decreased (improved), levels of *Sporacetigenium* also decreased. We similarly found that change in insulin was significantly positively correlated with change in *Sporacetigenium* in the ELD ($r=0.6689$, $p=0.001743$) and this correlation trended towards significance in the MID ($r=0.4360$, $p=0.08028$).

Finally, we asked whether baseline levels of *Sporacetigenium* were correlated with either blood glucose or insulin levels in the general population (ie. MID and ELD, placebo and MSPrebiotic groups before randomization and treatment). While there was no correlation between *Sporacetigenium* levels and blood glucose ($r=-0.0511$, $p=0.6639$), *Sporacetigenium* levels showed a significant positive correlation with insulin levels in the general population ($r=0.3371$, $p=0.003102$). Given that elevated insulin levels are indicative of developing insulin resistance, the major risk factor in developing Type 2 Diabetes, these findings demonstrate that *Sporacetigenium* levels represent a marker of microbiome dysbiosis linked to metabolic dysfunction that is sensitive to gut microbiome interventions.

Figure 3:
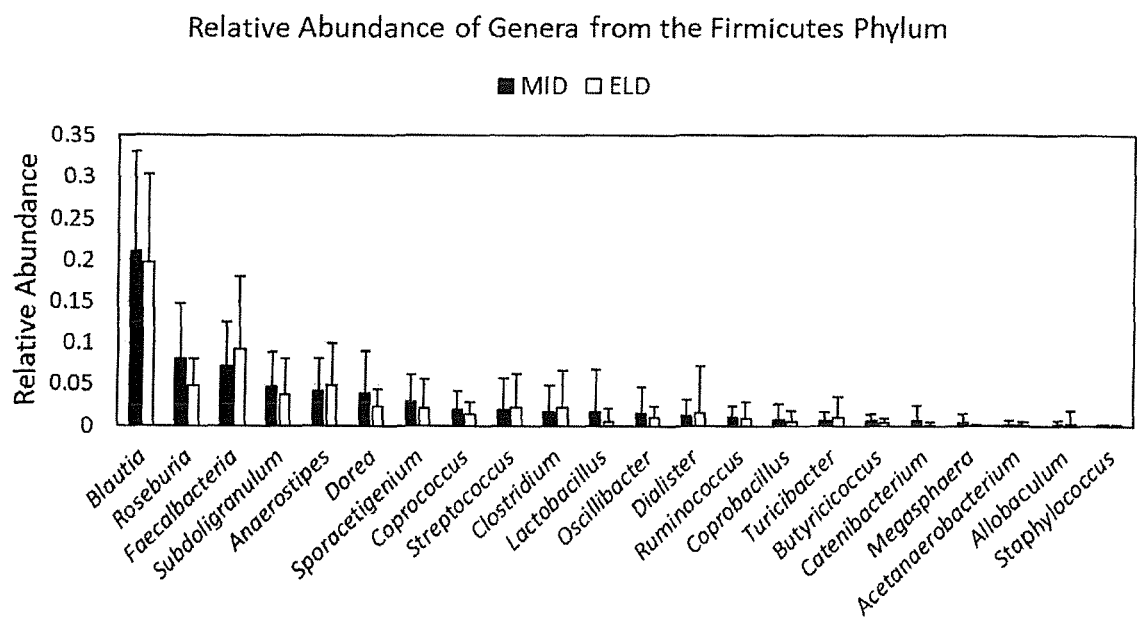
FIG. 3. Relative abundance of genera belonging to phylum Firmicutes in both MID and ELD cohorts at baseline expressed as a proportion of all counts demonstrates similarity in genus abundance between both groups. Specifically, the relative abundance of each genus belonging to the phylum Firmicutes at baseline is depicted for both middle-aged (30-50 years, MID; N=40) and elderly cohorts (>70 years, ELD; N=35) as the proportion of all counts (mean+/−standard deviation).
Figure 4:
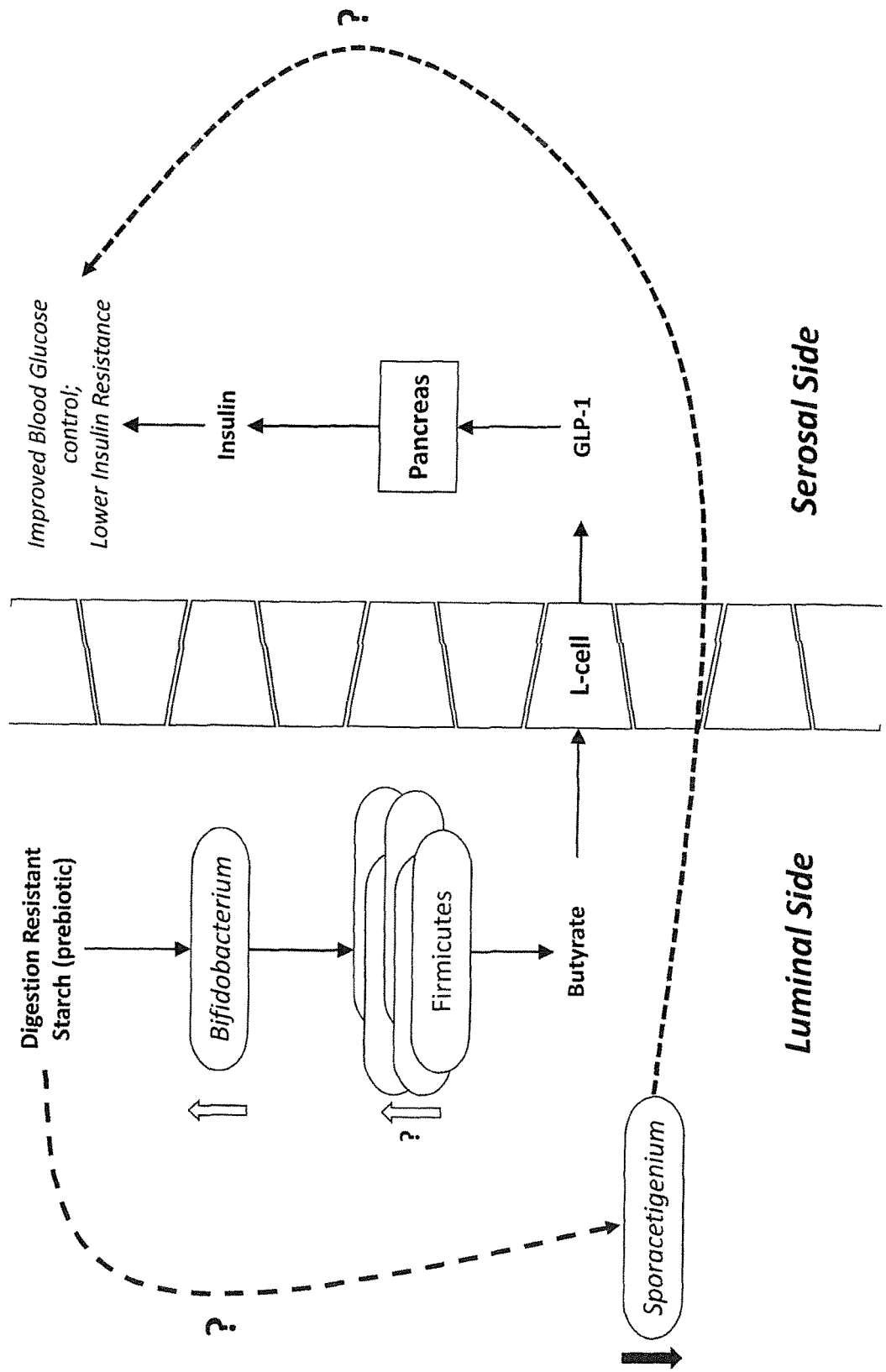
FIG. 4. Non-butyrate-producing genus *Sporacetigenium* of phylum Firmicutes influences metabolic parameters via mechanisms that may or may not Involve the prebiotic-Firmicutes-butyrate pathway. Individuals with decreasing *Sporacetigenium* levels and improvements in metabolic parameters in response to microbiome therapeutics, including prebiotic supplementation with resistant potato starch, have metabolic impairments linked to gut microbiome dysbiosis. The connections between decreasing *Sporacetigenium* levels, improved metabolism, and microbiome therapeutics remain to be elucidated.

These results are unexpected because, unlike most genera of the Firmicutes phylum, *Sporacetigenium* does not produce butyrate and does not ferment starch (Chen et al. 2006) and is not expected to influence metabolism in response to prebiotic supplementation. In fact, *Sporacetigenium* is a poorly characterized genus, making it difficult to explain the correlation between levels of this genus and metabolic function. Despite this, *Sporacetigenium* is a relatively common member of the gut microbiome, accounting for 2.1% of the population in the ELD and 2.8% of the population in the MID at baseline (FIG. 3).

*Sporacetigenium* was originally identified from strains isolated from an anaerobic digester treating municipal waste and sewage in Fujian, China (Chen et al. 2016). While very little is known about *Sporacetigenium*, levels of this genus have been found to increase in response to *Lactobacillus plantarum* probiotic supplementation in humans (Kwok et al. 2015), infections with *Salmonella enterica* and *Lawsonia intracellularis* in pigs (Borewicz et al. 2015), and high fat diets in mice (Nobel et al. 2015). *Sporacetigenium* hydrolyzes starch and major in vitro glucose fermentation products include acetate, ethanol, $H_2$ and $CO_2$ (Chen et al. 2016). *Sporacetigenium* produces $H_2S$ and $NH_4$ when cultured in peptone-yeast-glucose (PYG) broth (Chen et al. 2016).

While not wishing to be bound to a particular theory or hypothesis, *Sporacetigenium*, which readily ferments glucose and other simple sugars (Chen et al. 2016), may flourish in the gut microbiome under conditions of developing insulin resistance where such sugars are more abundant and elevated levels of *Sporacetigenium* may reflect a state of microbiome dysbiosis associated with metabolic dysfunction.

Alternatively, the noxious fermentation products produced by *Sporacetigenium*, including $H_2S$ and $NH_4$, may lead to low levels of inflammation, which is often associated with the development of insulin resistance (van Niekerk and Engelbrecht. 2018). In such a scenario, high *Sporacetigenium* levels may directly contribute to impaired insulin signaling and glucose homeostasis, and increased proliferation of healthy bacteria such as *Bifidobacterium* in response to microbiome therapeutics could out-compete and thereby improve the metabolism of the host by reducing the abundance of *Sporacetigenium*.

Yet another possibility includes the possibility that *Sporacetigenium* is supported by cross-feeding events produced within the gut microbiome during conditions of poor blood glucose and/or insulin homeostasis, and that *Sporacetigenium* levels are only indirectly associated with (ie. Do not influence) metabolic parameters.

Thus, as discussed above, gut microbiome dysbiosis contributes to pre-diabetes and type 2 diabetes. Surprisingly, changes in *Sporacetigenium* levels serves as a marker for changes in the pre-diabetic or type 2 diabetes state. Specifically, it is believed that *Sporacetigenium* levels serve as a marker of type 2 diabetes but are not a driver of microbiome-related metabolism. Accordingly, monitoring *Sporacetigenium* levels with at least one type 2 diabetes related parameter or type 2 diabetes related parameter provides information on the effectiveness of gut microbiome related treatments. If *Sporacetigenium* levels decrease in combination with one or more of the type 2 diabetes related parameters, this indicates that the individual can be treated using gut microbiome. Alternatively, if *Sporacetigenium* levels decrease but the type 2 diabetes related parameters do not, the type 2 diabetes disease progression may be more heavily influenced by other factors, for example, genetic predisposition, diet, activity levels or the like and the gut microbiome modulating treatment should be stopped and replaced with more conventional treatments for Type 2 diabetes.

In summary, screening for *Sporacetigenium* levels in combination with metabolic measures will identify those individuals who will benefit from positive modulation of the gut microbiome. The effectiveness of this strategy can then be measured by monitoring *Sporacetigenium* levels in combination with metabolic measures. Our findings support these statements for the following reasons: 1) Changes in *Sporacetigenium* and changes in blood glucose were positively correlated in those consuming the prebiotic supplement but not the placebo in both age groups, 2) similar correlations were detected between decreases in *Sporacetigenium* and reductions in insulin levels, and 3) *Sporacetigenium* levels are correlated with insulin levels in the general population.

This screen holds several advantages over methods focused on identifying and increasing beneficial bacteria as a means of improving metabolic measures. Given the complexity and individualized nature of the gut microbiome, minimum threshold levels of healthy bacteria necessary for proper metabolic functions cannot be determined because overlapping and complementary roles exist to promote a robust redundancy for the functions of the gut microbiome. This is likely why we were unable to identify a clear signal linking healthy bacteria to improvements in blood glucose and/or insulin: Despite specifically looking for these correlations, the microbial ecosystem linking prebiotic function and metabolic improvements varied too greatly between individuals, preventing their detection.

While other measures focus on ratios, like increasing the Firmicutes-to-Bacteroidetes proportions to promote metabolic health, our data reveal that phylum level comparisons are too coarse, lacking the detail required to make predictions. For example, it is possible that increasing levels of *Sporacetigenium*, a genus belonging to the Firmicutes phylum, could 'favourably' increase the Firmicutes-to-Bacteroidetes ratio, but our findings suggest that this would be counterproductive, as elevated *Sporacetigenium* is associated with unfavourable metabolic measures.

The gut microbiome is exceedingly complex and its influence on human physiology multifactorial. While other studies have found correlations between diabetic parameters and specific bacteria, this is the first screen that monitors the levels of a genus of bacteria whose levels decrease in individuals positively responding to microbiome-targeted lowering of insulin resistance. Other screens measure abundance of 'healthy' bacteria but neither minimum nor maximum effective levels are known. By monitoring the reduction of a bacterium, regardless of the level at baseline, as a proportion or actual count number, our data support the conclusion that reductions in *Sporacetigenium* in response to a microbiome-targeted therapeutic (a prebiotic, in our case) are correlated with improvements in both fasting blood glucose and insulin levels. This provides a generic method by which to test the efficacy of microbiome-based therapies for the lowering of blood glucose and/or insulin, and, by extension, reducing HbA1C, lowering insulin resistance, reversing prediabetes, preventing the onset of T2D, and/or improving the prognosis for those with T2D.

The invention will now be further explained and/or elucidated by way of examples; however, the invention is not necessarily limited to or by the examples.

Example 1—Materials and Methods

Clinical Study, Sample Collection, and Processing

Adults aged 30-50 years (middle-aged cohort; MID; 42 enrolled) or aged 70 years or older (elderly cohort; ELD; 42 enrolled) consumed 30 g per day of placebo (digestible corn starch; Amioca TF, Ingredion, Brampton, ON) for two weeks before being randomized to placebo or MSPrebiotic (digestion resistant potato starch (DRS); MSPrebiotics Inc., Carberry, MB) arms (Alfa et al. 2018a, Alfa et al. 2018b). Participants then consumed 30 g of placebo or DRS daily for 12 weeks (14 weeks total). Stool and fasting blood samples were collected at baseline and 14 weeks. Prediabetics and diabetics were excluded based on enrollment screening. Antibiotic treatment alters the microbiome, so only samples from participants who did not receive antibiotic treatment within 5 weeks of stool sample collection were analyzed (MID=40, ELD 35). Blood glucose levels were determined by Diagnostic Services Manitoba (Winnipeg, MB) and insulin levels by LipoScience Inc. (Raleigh, NC). Gut microbiome analysis was performed by 16S sequencing on the Illumina MiSeq platform and alignment as previously described (Alfa et al. 2018a, Schloss et al. 2009, Kozich et al. 2013).

Statistical Analysis

Baseline values were subtracted from week 14 values and expressed as a change in percent (blood glucose and insulin levels) or a change in relative abundance (bacteria) for each participant. Pearson's correlation coefficients (r) and p values for changes in Firmicutes genera and change in blood glucose in both the MID and ELD cohorts consuming DRS were calculated using Excel (Microsoft, Redmond, WA). Significance was determined using the Benjamini-Hochberg procedure (Benajmini and Hochberg. 1995) at a false discovery rate (FDR; q) of 0.1. The critical values for each genus were generated by dividing the p value rank (i) by the total number of genera analyzed (m), then multiplying this quotient by the FDR (q). Pearson's correlation coefficients and p values were calculated using Excel for select changes in Firmicutes genera and changes in insulin levels. Correlations between change in genus abundance and change in insulin level were considered significant at p<0.05.

REFERENCES

M. J. Alfa, D. Strang, P. S. Tappia, M. Graham, G. Van Domselaar, J. D. Forbes, V. Laminman, N. Olson, P. DeGagne, D. Bray, B.-L. Murray, B. Dufault and L. M. Lix, "A randomized trial to determine the impact of a digestion resistant," Clinical Nutrition, vol. 37, no. 3, pp. 797-807, 2018a.

M. J. Alfa, D. Strang, P. S. Tappia, N. Olson, P. DeGagne, D. Bray, B.-L. Murray and B. Hiebert, "A Randomized Placebo Controlled Clinical Trial to Determine the Impact of Digestion Resistant Starch MSPrebiotic on Glucose, Insulin, and Insulin Resistance in Elderly and Mid-Age Adults," Fronteirs in Medicine (Lausanne), vol. 4, p. 260, 2018b.

Belenguer A, Duncan S H, Calder A G, Holtrop G, Louis P, Lobley G E, Flint H J. Two routes of metabolic cross-feeding between *Bifidobacterium adolescentis* and butyrate-producing anaerobes from the human gut. Appl Environ Microbiol. 2006 May; 72(5):3593-9.

Y. Benjamini and Y. Hochberg, "Controlling the False Discovery Rate: A Practical and Powerful Approach to Multiple Testing," Journal of the Royal Statistical Society. Series B (Methodological), vol. 57, no. 1, pp. 289-300, 1995.

K. A. Borewicz, H. B. Kim, R. S. Singer, C. J. Gebhart, S. Sreevatsan, T. Johnson and R. E. Isaacson, "Changes in the Porcine Intestinal Microbiome in Response to Infection with *Salmonella enterica* and *Lawsonia intracellularis*," PLoS ONE, vol. 10, no. 10, p. e0139106, 2015.

Brown K, DeCoffe D, Molcan E, Gibson D L Diest-induced dysbiosis of the microbiota and the effects on immunity and disease. Nutrients 2012; 4:1095-1119, DOI: 10.3390/nu4081095.

E. E. Canfora, C. M. van der Beek, G. D. A. Hermes, G. H. Goossens, J. W. E. Jocken, J. J. Hoist, H. M. Van Eijk, K. Venema, H. Smidt, E. G. Zoetendal, C. H. C. Dejong, K. Lenaerts and E. E. Blaak, "Supplementation of Diet With Galacto-oligosaccharides Increases Bifidobacteria, but Not Insulin Sensitivity, in Obese Prediabetic Individuals," Gastroenterology, vol. 153, no. 1, pp. 87-97, 2017.

Cecchini D A, Laville E, Laguerre S, Robe P, Leclerc M, Dore J, Henrissat B, Remaud-Simeon M, Monsan P, Potocki-Veronese G Functional metagenomics reveals novel pathways of prebiotic breakdown in human gut bacteria. PLOS one 2013; 8:e72766. Doi:10.1371/journal.pone.0072766.

S. Chen, L. Song and X. Dong, "*Sporacetigenium mesophilum* gen. nov., sp. nov., isolated from an anaerobic digester treating municipal solid waste and sewage," International Journal of Systematic and Evolutionary Microbiology, vol. 56, no. Pt 4, pp. 721-5, 2006.

D. W. K. N. M. Cockburn, "Polysaccharide Degradation by the Intestinal Microbiota and Its Influence on Human Health and Disease," J Mol Biol, no. 428, pp. 3230-3252, 2016.

Flint H J, Scott K P, Duncan S H, Louis P, Forano E. Microbial degradation of complex carbohydrates in the gut. Gut Microbes 2012; 34:289-306.

Hardy H, Harris J, Lyon E, Beal J, Foey A D Probiotics, prebiotics and immunomodulation of gut mucosal defences: homeostasis and immunopathology. Nutrients 2013; 5:1869-1912, doi:10.3390/nu5061869.

Holmes E, Kinross J, Gibson G R, Burcelin R, Jia W, Pettersson S, Nicholson J K Therapeutic modulation of microbiota-host metabolic interactions. Sci Transl Med 2012; 4:137rv6DOI: 10.1126/scitranslmed.3004244.

H. D. Holscher, "Dietary fiber and prebiotics and the gastrointestinal microflora," Gut Microbes, vol. 8, no. 2, pp. 172-184, 2017.

J. J. Kozich, S. L. Westcott, N. T. Baxter, S. K. Highlander and P. D. Schloss, "Development of a dual-index sequencing strategy and curation pipeline for analyzing amplicon sequence data on the MiSeq Illumina sequencing platform," Applied and Environmental Microbiology, vol. 79, no. 17, pp. 5112-20, 2013.

H. V. Lin, A. Frassetto, E. J. Kowalik, A. R. Nawrocki, M. M. Lu, J. R. Kosinski, J. A. Hubert, D. Szeto, X. Yao, G. Forrest and D. Marsh, "Butyrate and Propionate Protect against Diet-Induced Obesity and Regulate Gut Hormones via Free Fatty Acid Receptor 3-Independent Mechanisms," PLoS ONE, vol. 7, no. 4, p. e35240, 2016.

L. Y. Kwok, Z. Guo, J. Zhang, L. Wang, J. Qiao, Q. Hou, Y. Zheng and H. Zhang, "The impact of oral consumption of *Lactobacillus plantarum* P-8 on faecal bacteria revealed by pyrosequencing," Beneficial Microbes, vol. 6, no. 4, pp. 405-13, 2015.

S. Macfarlane and G. T. Macfarlane, "Regulation of short-chain fatty acid production," Proceedings of the Nutrition Society, vol. 62, no. 1, pp. 67-72, 2003.

Malaguarnera A, Leggio F, Vacante M, Motta M, Giordano M, Biondi A Basile F, Mastronjeni S, Mistretta A, Malaguarnera M Toscano M A, Salmeri M Probiotics in the gastrointestinal diseases of the elderly. J Nutr Health Aging. 16:4. pp 402-410. 2012.

D. Mariat, O. Firmesse, F. Levenez, V. Guimaraes, H. Sokol, J. Dore, G. Corthier and J. Furet, "The Firmicutes/Bacteroidetes ratio of the human microbiota changes with age," BMC Microbiology, vol. 9, p. 123, 2009.

Y. R. Nobel, L. M. Cox, F. F. Kirigin, N. A. Bokulich, S. Yamanishi, I. Teitler, J. Chung, J. Sohn, C. M. Barber, D. S. Goldfarb, K. Raju, S. Abubucker, Y. Zhou, V. E. Ruiz, H. Li, M. Mitreva, A. V. Alekseyenko, G. M. Weinstock, E. Sodergren and M. J. Blaser, "Metabolic and metagenomic outcomes from early-life pulsed antibiotic treatment," Nature Communications, vol. 6, p. 7486, 2015.

T. C. Rideout, S. V. Harding, A. Raslawsky and C. B. Rempel, "Dietary Resistant Starch Supplementation Increases High-Density Lipoprotein Particle Number in Pigs Fed a Western Diet," Journal of Dietary Supplements, vol. 14, no. 3, pp. 334-345, 2017.

I. Rowland, G. Gibson, A. Heinken, K. Scott, J. Swann, I. Thiele and K. Tuohy, "Gut microbiota functions: metabolism of nutrients and other food components," European Journal of Nutrition, vol. 57, pp. 1-24, 2018.

Royall D, Wolever T M & Jeejeebhoy K N (1990) Clinical significance of colonic fermentation. Am J Gastroenterol. 85, 1307-1312

P. D. Schloss, S. L. Westcott, T. Ryabin, J. R. Hall, M. Hartmann, E. B. Hollister, R. A. Lesniewski, B. B. Oakley, D. H. Parks, C. J. Robinson, J. W. Sahl, B. Stres, G. G. Thallinger, D. J. van Horn and C. F. Weber, "Introducing mothur: open-source, platform-independent, community-supported software for describing and comparing microbial communities," Applied and Environmental Microbiology, vol. 75, no. 23, pp. 7537-7541, 2009.

Topping D L, Clifton P M Short-chain fatty acids and human colonic function: Roles of resistant starch and nonstarch polysaccharides Physiological Reviews 2001; 81:1031-1064

Toward R E, Montandon S L, Walton G E, Gibson G R Effect of prebiotics on the human gut microbiota of elderly persons. Gut Microbes 2012; 3:57-60 DOI: 10.4161/gmic.19411 van Niekerk and Engelbrecht. Cytokine Growth Factor Rev. 2018 Jun. 28. pii: S1359-6101 (18)30065-0. doi: 10.1016/j.cytogfr.2018.06.003. [Epub ahead of print] Inflammation-induced metabolic derangements or adaptation: An immunometabolic perspective.

TABLE 1

Correlations between the change in abundance of Firmicutes genera and change in blood glucose levels in ELD consuming DRS.

| Firmicutes Genera | r | p value | Rank | [i/m] * q | Significant |
|---|---|---|---|---|---|
| Sporacetigenium | 0.637197 | 0.003349 | 1 | — | Y |
| Butyricicoccus | −0.59212 | 0.007578 | 2 | 0.009091 | Y |
| Dorea | −0.5141 | 0.024367 | 3 | 0.013636 | N |
| Dialister | 0.466132 | 0.04428 | 4 | 0.018182 | N |
| Subdoligranulum | −0.43243 | 0.064739 | 5 | 0.022727 | N |
| Ruminococcus | −0.42343 | 0.071162 | 6 | 0.027273 | N |
| Acetanaerobacterium | −0.3212 | 0.180244 | 7 | 0.031818 | N |
| Staphylococcus | 0.314391 | 0.190026 | 8 | 0.036364 | N |
| Coprococcus | −0.2843 | 0.238659 | 9 | 0.040909 | N |
| Oscillibacter | −0.242 | 0.318192 | 10 | 0.045455 | N |
| Coprobacillus | −0.19932 | 0.414072 | 11 | 0.05 | N |
| Allobaculum | −0.17033 | 0.486556 | 12 | 0.054545 | N |
| Faecalibacterium | −0.16854 | 0.491773 | 13 | 0.059091 | N |
| Streptococcus | 0.154658 | 0.527417 | 14 | 0.063636 | N |
| Blautia | −0.14803 | 0.545401 | 15 | 0.068182 | N |
| Megasphaera | −0.12762 | 0.604386 | 16 | 0.072727 | N |
| Catenibacterium | −0.11985 | 0.627517 | 17 | 0.077273 | N |
| Roseburia | −0.11539 | 0.63921 | 18 | 0.081818 | N |
| Anaerostipes | −0.07749 | 0.754042 | 19 | 0.086364 | N |
| Turicibacter | 0.045048 | 0.854856 | 20 | 0.090909 | N |
| Clostridium | 0.005995 | 0.980875 | 21 | 0.095455 | N |
| Lactobacillus | 0.000969 | 0.997082 | 22 | 0.1 | N |

The Benjamini-Hochberg method was employed to control for false discovery of significant correlations. Results are rank ordered based on p value, and the p value is compared to the critical value ([i/m] * q, FDR = 0.1) beginning with the lowest ranking genus (Lactobacillus). The first correlation with a p value lower than the critical value (Butyricicoccus) and all higher-ranking correlations (Sporacetigenium) are considered significant. Positive Pearson correlation coefficient (r) values indicate positive correlations and negative r values indicate negative correlations.

TABLE 2

Correlations between the change in abundance of Firmicutes genera and change in blood glucose levels in MID consuming DRS.

| Firmicutes Genera | r | p value | Rank | [i/m] * q | Significant |
|---|---|---|---|---|---|
| Anaerostipes | −0.59026 | 0.007836 | 1 | — | Y |
| Sporacetigenium | 0.572948 | 0.010351 | 2 | — | Y |
| Roseburia | 0.55731 | 0.013178 | 3 | 0.013636 | Y |
| Catenibacterium | 0.420061 | 0.073405 | 4 | 0.018182 | N |
| Lactobacillus | −0.41106 | 0.080448 | 5 | 0.022727 | N |
| Turicibacter | 0.367908 | 0.121212 | 6 | 0.027273 | N |
| Dialister | −0.34296 | 0.151806 | 7 | 0.031818 | N |
| Clostridium | 0.339875 | 0.15463 | 8 | 0.036364 | N |
| Oscillibacter | 0.31535 | 0.188544 | 9 | 0.040909 | N |
| Allobaculum | 0.307439 | 0.200465 | 10 | 0.045455 | N |
| Streptococcus | 0.196132 | 0.421046 | 11 | 0.05 | N |
| Coprococcus | −0.13959 | 0.57036 | 12 | 0.054545 | N |
| Coprobacillus | 0.136678 | 0.577099 | 13 | 0.059091 | N |
| Megasphaera | −0.11576 | 0.63921 | 14 | 0.063636 | N |
| Faecalibacterium | −0.11283 | 0.648034 | 15 | 0.068182 | N |
| Blautia | 0.095377 | 0.697952 | 16 | 0.072727 | N |
| Ruminococcus | −0.05663 | 0.819876 | 17 | 0.077273 | N |
| Subdoligranulum | −0.05359 | 0.829386 | 18 | 0.081818 | N |
| Butyricicoccus | 0.050646 | 0.837011 | 19 | 0.086364 | N |
| Acetanaerobacterium | 0.040254 | 0.870206 | 20 | 0.090909 | N |
| Staphylococcus | 0.040016 | 0.870846 | 21 | 0.095455 | N |
| Dorea | −0.01964 | 0.938462 | 22 | 0.1 | N |

The Benjamini-Hochberg method was employed to control for false discovery of significant correlations. Results are rank ordered based on p value, and the p value is compared to the critical value ([i/m] * q, FDR = 0.1) beginning with the lowest ranking genus (Dorea). The first correlation with a p value lower than the critical value (Roseburia) and all higher-ranking correlations (Sporacetigenium, Anaerostipes) are considered significant. Positive Pearson correlation coefficient (r) values indicate positive correlations and negative r values indicate negative correlations.

The invention claimed is:

1. A method for determining efficacy of a microbiome modulating treatment for high blood glucose or high blood insulin levels in an individual at risk of developing type 2 diabetes or who has developed type 2 diabetes or who has type 2 diabetes, said method comprising:

detecting Sporacetigenium levels in a first gut microbiome sample from the individual at a first time point;

determining a first measurement of a type 2 diabetes related parameter of the individual at the first time point;

administering to the individual an effective amount of a gut microbiome modulating treatment on a dosage regimen or schedule for a suitable period of time;

following the suitable period of time, obtaining a second gut microbiome sample from the individual;

detecting Sporacetigenium levels in the second sample;

determining a second measurement of the type 2 diabetes related parameter of the individual at the second time point;

comparing Sporacetigenium levels in the second gut microbiome sample to Sporacetigenium levels in the first gut microbiome sample, and comparing the first measurement of the type 2 diabetes related parameter and the second measurement of the type 2 diabetes related parameter, wherein if the Sporacetigenium levels in the second sample are lower than Sporacetigenium levels in the first sample and the second type 2 diabetes related parameter is lower than the first type 2 diabetes related parameter, continuing the dosage regimen for the individual.

2. The method according to claim 1 wherein the individual who is at risk of developing type 2 diabetes is at risk based on genetic predisposition, familial history, heredity, lifestyle or one or more type 2 diabetes related parameters being elevated.

3. The method according to claim 1 wherein the microbiome modulating treatment is selected from the group consisting of: resistant potato starch, probiotic genera, species, and strains; prebiotics supporting growth of probiotic genera, species and strains; resistant starch from corn, tapioca, banana, grains, and tubers; fructooligosaccharides; galactooligosaccharides; xylooligosaccharides; mannanoligosaccharides; arabinoxylooligosaccharides; arabinogalactan polysaccharides; galactomannan polysaccharides; dietary changes that support the growth of probiotic bacteria; dietary treatments that reduce the availability of glucose and/or fructose and/or other fermentation substrates to Sporacetigenium in the digestive tract; antibiotics that target Sporacetigenium or another bacterium/other bacteria that facilitate the growth of Sporacetigenium; mixed plant cell wall fibers; beta-glucans; resistant dextrins; resistant maltodextrins; limit dextrins; polydextrose; alginate; pectin polysaccharides; hydroxypropylmethylcellulose; chitin; chondroitin-containing compounds; and glucosamine-containing compounds.

4. The method according to claim 1 wherein the type 2 diabetes related parameter is selected from the group consisting of: insulin levels; fasting blood glucose levels; insulin resistance levels; and HbA1C levels.

5. The method according to claim 1 wherein the suitable period of time is from 1 week to 6 months.

6. The method according to claim 1 wherein Sporacetigenium levels are measured by using a method selected from the group consisting of: real-time polymerase chain reaction (RT-PCR)-based methods; qualitative PCR (qPCR) based methods; microbiome sequencing; shotgun metagenomic sequencing; quantitative fluorescent in situ hybridization (FISH); antibody-based methods; and cell-binding based methods.

7. The method according to claim 1 wherein the gut microbiome modulating treatment is resistant potato starch.

8. The method according to claim 7 wherein the effective amount is 2 to 40 g per day of resistant potato starch.

9. A method for determining efficacy of a microbiome modulating treatment for high blood glucose or high blood insulin levels in an individual at risk of developing or who has developed or who has type 2 diabetes, said method comprising:
  detecting *Sporacetigenium* levels in a first gut microbiome sample from the individual at a first time point;
  administering to the individual a microbiome modulating treatment on a dosage regimen for a suitable period of time;
  following the suitable period of time, obtaining a second gut microbiome sample from the individual;
  detecting *Sporacetigenium* levels in the second sample; and
  comparing *Sporacetigenium* levels in the second gut microbiome sample to *Sporacetigenium* levels in the first gut microbiome sample,
  wherein if the *Sporacetigenium* levels in the second sample are lower than *Sporacetigenium* levels in the first sample, continuing the dosage regimen for the individual.

10. The method according to claim 9 wherein at the first time point and the second time point, at least one type 2 diabetes related parameter of the individual is measured and these two parameters are also compared.

11. The method according to claim 9 wherein the individual who is at risk of developing type 2 diabetes is at risk based on genetic predisposition, familial history, heredity, lifestyle or one or more type 2 diabetes related parameters being elevated.

12. The method according to claim 9 wherein the microbiome modulating treatment is selected from the group consisting of: resistant potato starch, probiotic genera, species, and strains; prebiotics supporting growth of probiotic genera, species and strains; resistant starch from corn, tapioca, banana, grains, and tubers; fructooligosaccharides; galactooligosaccharides; xylooligosaccharides; mannanoligosaccharides; arabinoxylooligosaccharides; arabinogalactan polysaccharides; galactomannan polysaccharides; dietary changes that support the growth of probiotic bacteria; dietary treatments that reduce the availability of glucose and/or fructose and/or other fermentation substrates to *Sporacetigenium* in the digestive tract; antibiotics that target *Sporacetigenium* or another bacterium/other bacteria that facilitate the growth of *Sporacetigenium*; mixed plant cell wall fibers; beta-glucans; resistant dextrins; resistant maltodextrins; limit dextrins; polydextrose; alginate; pectin polysaccharides; hydroxypropylmethylcellulose; chitin; chondroitin-containing compounds; and glucosamine-containing compounds.

13. The method according to claim 10 wherein the type 2 diabetes related parameter is selected from the group consisting of: insulin levels; fasting blood glucose levels; insulin resistance levels; and HbA1C levels.

14. The method according to claim 9 wherein the suitable period of time is from 1 week to 6 months.

15. The method according to claim 9 wherein *Sporacetigenium* levels are measured by using a method selected from the group consisting of: real-time polymerase chain reaction (RT-PCR)-based methods; qualitative PCR (qPCR) based methods; microbiome sequencing; shotgun metagenomic sequencing; quantitative fluorescent in situ hybridization (FISH); antibody-based methods; and cell-binding based methods.

16. The method according to claim 9 wherein the gut microbiome modulating treatment is resistant potato starch.

17. The method according to claim 16 wherein the effective amount is 2 to 40 g per day of resistant potato starch.

18. A method for monitoring efficacy of a gut microbiome modulating treatment for high blood glucose or high blood insulin levels in an individual being administered said microbiome modulating treatment, said method comprising:
  detecting *Sporacetigenium* levels in a first gut microbiome sample from the individual at a first time point;
  following a suitable period of time, obtaining a second gut microbiome sample from the individual;
  detecting *Sporacetigenium* levels in the second sample; and
  comparing *Sporacetigenium* levels in the second gut microbiome sample to *Sporacetigenium* levels in the first gut microbiome sample,
  wherein if the *Sporacetigenium* levels in the second sample are lower than *Sporacetigenium* levels in the first sample, the microbiome modulating treatment is effective.

19. A method for determining efficacy of a gut microbiome modulating treatment for high blood glucose or high blood insulin levels in an individual being administered said microbiome modulating treatment, said method comprising:
  detecting *Sporacetigenium* levels in a first gut microbiome sample from the individual at a first time point;
  determining a first measurement of a type 2 diabetes related parameter of the individual at the first time point;
  following a suitable period of time, obtaining a second gut microbiome sample from the individual;
  detecting *Sporacetigenium* levels in the second sample;
  determining a second measurement of the type 2 diabetes related parameter of the individual at the second time point;
  comparing *Sporacetigenium* levels in the second gut microbiome sample to *Sporacetigenium* levels in the first gut microbiome sample, and
  comparing the first measurement of the type 2 diabetes related parameter and the second measurement of the type 2 diabetes related parameter,
  wherein if the *Sporacetigenium* levels in the second sample are lower than *Sporacetigenium* levels in the first sample and the second measurement of the type 2 diabetes related parameter is lower than the first measurement of the type 2 diabetes related parameter, the gut microbiome modulating treatment is effective.

* * * * *